United States Patent
Bristow (10) Patent No.: US 9,546,120 B2
(45) Date of Patent: *Jan. 17, 2017

(54) INTEGRATED PROCESS FOR THE PRODUCTION OF METHANOL AND METHYL ACETATE

(71) Applicant: BP Chemicals Limited, Middlesex (GB)

(72) Inventor: Timothy Crispin Bristow, East Yorkshire (GB)

(73) Assignee: BP CHEMICALS LIMITED, Middlesex (GB)

(*) Notice: Subject to any disclaimer, the term of this patent is extended or adjusted under 35 U.S.C. 154(b) by 20 days.

This patent is subject to a terminal disclaimer.

(21) Appl. No.: 14/650,902

(22) PCT Filed: Dec. 19, 2013

(86) PCT No.: PCT/EP2013/077462
§ 371 (c)(1),
(2) Date: Jun. 10, 2015

(87) PCT Pub. No.: WO2014/096237
PCT Pub. Date: Jun. 26, 2014

(65) Prior Publication Data
US 2015/0329450 A1    Nov. 19, 2015

(30) Foreign Application Priority Data

Dec. 21, 2012  (EP) .................................... 12199087

(51) Int. Cl.
| | | |
|---|---|---|
| *C07C 29/151* | (2006.01) | |
| *C07C 67/37* | (2006.01) | |
| *C07C 51/09* | (2006.01) | |

(52) U.S. Cl.
CPC ............ *C07C 29/1518* (2013.01); *C07C 51/09* (2013.01); *C07C 67/37* (2013.01); *Y02P 20/125* (2015.11)

(58) Field of Classification Search
CPC .......... C07C 67/37; C07C 29/151; C07C 41/16
See application file for complete search history.

(56) References Cited

U.S. PATENT DOCUMENTS

| | | | |
|---|---|---|---|
| 5,502,243 A | 3/1996 | Waller et al. | |
| 2006/0252959 A1 | 11/2006 | Cheung et al. | |
| 2010/0121098 A1* | 5/2010 | Ditzel ..................... | B01J 29/20 560/232 |

FOREIGN PATENT DOCUMENTS

| | | |
|---|---|---|
| EP | 0 529 868 A2 | 3/1993 |
| EP | 0 566 370 A2 | 10/1993 |
| EP | 0566370 A2 * | 10/1993 |
| EP | 0 801 050 A1 | 10/1997 |
| EP | 2 559 680 A1 | 2/2013 |
| GB | 1 306 863 A | 2/1973 |
| GB | 1306863 * | 2/1973 |
| WO | WO 03/097523 A2 | 11/2003 |

* cited by examiner

*Primary Examiner* — Paul A Zucker
(74) *Attorney, Agent, or Firm* — Nixon & Vanderhye P.C.

(57) ABSTRACT

Integrated process for the production of methyl acetate and methanol by carbonylating dimethyl ether with synthesis gas, recovering a methyl acetate stream and an unreached synthesis gas stream containing methyl acetate, and scrubbing the synthesis gas to remove methyl acetate. The scrubbed synthesis gas is passed for methanol synthesis.

30 Claims, 3 Drawing Sheets

INTEGRATED PROCESS FOR THE PRODUCTION OF METHANOL AND METHYL ACETATE

This application is the U.S. national phase of International Application No. PCT/EP2013/077462 filed Dec. 19, 2013 which designated the U.S. and claims priority to European Patent Application No. 12199087.3 filed Dec. 21, 2012, the entire contents of each of which are hereby incorporated by reference.

The present invention relates to an integrated process for the production of methyl acetate and methanol from synthesis gas and dimethyl ether.

BACKGROUND OF THE INVENTION

Methanol is primarily used to produce formaldehyde, methyl tertiary butyl ether (MTBE) and acetic acid, with smaller amounts going into the manufacture of dimethyl terephthalate (DMT), methylmethacrylate (MMA), chloromethanes, methylamines, glycol methyl ethers, and fuels. It also has many general solvent and antifreeze uses, such as being a component for paint strippers, car windshield washer compounds and a de-icer for natural gas pipelines A major use of methyl acetate is as a low toxicity solvent in glues, paints and a broad range of coating and ink resin applications. Methyl acetate also finds use as a feedstock in the production of acetic anhydride.

Methanol may be produced on a commercial basis by the conversion of synthesis gas containing carbon monoxide, hydrogen and optionally carbon dioxide over a suitable catalyst according to the overall reaction:

Widely used catalysts for methanol synthesis from synthesis gas are based on copper.

WO 03/097523 describes a plant and process that produces methanol and acetic acid under substantially stoichiometric conditions, wherein an unadjusted syngas having an R ratio less than 2.0 is provided. All or part of the unadjusted syngas is supplied to a separator unit to recover $CO_2$, CO and hydrogen. At least a portion of any one or combination of the recovered $CO_2$, CO and hydrogen is added to any remaining syngas not so treated or alternatively combines in the absence of any remaining unadjusted syngas to yield an adjusted syngas with an R ratio of 2.0 to 2.9 which is used to produce methanol. Any recovered CO2 not used to adjust the R ratio of the unadjusted syngas can be supplied to the reformer to enhance CO production. At least a portion of the recovered CO is reacted in the acetic acid reactor with at least a portion of the produced methanol to produce acetic acid or an acetic acid precursor by a conventional process.

Methyl acetate may be produced by an integrated process as described in EP-A-0529868, in which process methanol and acetic acid are reacted in an esterification reactor and the methyl acetate is recovered by distillation and the water by azeotropic distillation, the process is operated in 'standby' mode by shutting off the methanol and acetic acid feeds to the esterification reactor and recycling the methyl acetate and water to the esterification reactor so that the process may be rapidly restarted.

Methyl acetate may be produced, as described, for example in WO 2006/121778, by carbonylating dimethyl ether with carbon monoxide in the presence of a zeolite carbonylation catalyst, such as a mordenite zeolite.

The production of methyl acetate by the carbonylation of dimethyl ether may also be carried out using mixtures of carbon monoxide and hydrogen, as described, for example in WO 2008/132438. According to WO 2008/132438, the molar ratio of carbon monoxide:hydrogen for use in the carbonylation step may be in the range 1:3 to 15:1, such as 1:1 to 10:1, for example 1:1 to 4:1.

WO 01/07393 describes a process for the catalytic conversion of a feedstock comprising carbon monoxide and hydrogen to produce at least one of an alcohol, ether and mixtures thereof and reacting carbon monoxide with the at least one of an alcohol, ether and mixtures thereof in the presence of a catalyst selected from solid super acids, heteropolyacids, clays, zeolites and molecular sieves, in the absence of a halide promoter, under conditions of temperature and pressure sufficient to produce at least one of an ester, acid, acid anhydride and mixtures thereof.

EP-A-2559680 describes a carbonylation process for the production of acetic acid and/or methyl acetate by contacting in a carbonylation reactor carbon monoxide with a feed comprising methanol and/or a reactive derivative thereof in the vapour phase and in the presence of a heterogeneous catalyst comprising a heteropolyacid, wherein the heteropolyacid has been ion-exchanged or loaded with an organometallic complex of a Group VIII metal and at least one ligand, which ligand comprises one or more nitrogen and/or phosphorous donor atoms.

GB 1306863 describes a process for producing acetic acid, which comprises the following steps: (a) reacting a gaseous mixture of carbon monoxide and hydrogen in a molar ratio of 1:not more than 0.5, with methanol in the gas phase in the presence of a transition metal catalyst and a halogen-containing compound co-catalyst until no more than half of the carbon monoxide is consumed; (b) cooling the reacted gas obtained in step (a), separating the cooled gas into a liquid component containing acetic acid and a gaseous component containing unreacted carbon monoxide and hydrogen, and withdrawing the acetic acid from the reaction system; (c) washing the gaseous component from step (b) with cold methanol; and (d) reacting the washed gaseous component from step (c) in the presence of a copper-containing catalyst to yield methanol and passing this methanol to step (a).

U.S. Pat. No. 5,840,969 describes a process for the preparation of acetic acid comprising, in a first catalytic step, conversion of a hydrogen and carbon monoxide-containing synthesis gas to obtain a liquid process stream comprising methanol and, in a second catalytic step, carbonylation of the process stream with carbon monoxide to produce a product stream being rich in the acetic acid product in the presence of catalytic effective amounts of a metal compound selected from Group VIII of the Periodic Table promoted with a halide compound; withdrawing from the carbonylation step a vent gas stream comprising carbon monoxide and residual amounts of acetic acid and halide compound; separating the vent gas stream into a liquid fraction containing a part of the residual amounts of acetic acid and part of the halide compound, and a gaseous fraction with the carbon monoxide and remaining amounts of acetic acid and halide compound; recycling the liquid fraction to the carbonylation step; subjecting the gaseous fraction to liquid absorption to remove the acetic acid and halide compound in the gaseous fraction, to obtain a carbon monoxide rich recycle stream; and introducing the carbon monoxide rich recycle stream into the synthesis gas conversion step.

EP-A-0801050 describes a process for the preparation of acetic acid which comprises catalytic steps of converting hydrogen and carbon monoxide in the synthesis gas to a mixed process stream containing methanol and dimethyl ether and carbonylating methanol and dimethyl ether formed in the process stream into acetic acid.

U.S. Pat. No. 5,502,243 describes a process wherein oxygenated acetyl compounds ethylidene acetate, acetic acid, acetic anhydride, acetaldehyde and methyl acetate are produced directly from synthesis gas and dimethyl ether in a catalyzed liquid phase reaction system. The inclusion of carbon dioxide in the synthesis gas in selected amounts increases the overall yield of oxygenated acetyl compounds from the reactant dimethyl ether. When methanol is included in the reactor feed, the addition of carbon dioxide significantly improves the molar selectivity to ethylidene diacetate.

EP-A-0566370 describes a process for the production of ethylidene diacetate, acetic acid, acetic anhydride and methyl acetate directly from synthesis gas via an intermediate product stream containing dimethyl ether. Dimethyl ether is produced from synthesis gas in a first liquid phase reactor and the reactor effluent comprising dimethyl ether, methanol and unreacted synthesis gas flows to a second liquid phase reactor containing acetic acid in which the oxygenated acetyl compounds are synthesized catalytically. Vinyl acetate and additional acetic acid optionally are produced by pyrolysis of ethylidene diacetate in a separate reactor system. Synthesis gas is preferably obtained by partial oxidation of a hydrocarbon feedstock such as natural gas. Optionally a portion of the acetic acid co-product is recycled to the partial oxidation reactor for conversion into additional synthesis gas.

Synthesis gas comprises carbon monoxide and hydrogen. Optionally carbon dioxide is included. The synthesis gas ratio or stoichiometric number (SN) of a synthesis gas composition is conventionally calculated as $$SN=(H_2—CO_2)/(CO+CO_2)$$

wherein $H_2$, CO and $CO_2$ represent the composition of the gas on a molar basis.

Desirably, the optimum stoichiometric number of a synthesis gas for use in methanol production is 2.05. Typically, however, processes for the production of methyl acetate by the carbonylation of dimethyl ether with synthesis gas employ synthesis gas with a stoichiometric excess of carbon monoxide. Thus a major drawback in integrated carbonylation and methanol synthesis processes is that the hydrogen:carbon monoxide ratios desirable for methanol synthesis are significantly higher than the desired ratios for carbonylation.

A further drawback of processes for the carbonylation of dimethyl ether is that a purge gas must be removed from the process to prevent recycle components from reaching unacceptable levels in the reactor. Typically, purge gases are disposed of by burning. Purge gas from the carbonylation process contains carbon monoxide and invariably contains some dimethyl ether and methyl acetate. Therefore, the removal of these components by purging represents a loss of values and reduces the overall efficiency of the process.

A yet further drawback is that the introduction of synthesis gas streams containing methyl acetate to methanol synthesis processes has now been found to result in undesirable side-reactions and/or by-products, such as ethanol and acetic acid resulting in a detrimental loss of catalytic performance and/or methanol productivity.

As described above, processes for the carbonylation of dimethyl ether with synthesis gas typically employ synthesis gas with a stoichiometric excess of carbon monoxide. This results in unconsumed carbon monoxide being withdrawn (together with hydrogen which generally remains unconsumed in the process) from the process as part of the carbonylation product stream. Typically, to avoid loss of carbon monoxide feedstock from the process it is recycled together with the unconsumed hydrogen to the carbonylation reactor. A disadvantage of this is that hydrogen builds-up in the reactor and an undesirable reduction in the carbonylation reaction rate is observed.

Furthermore, due to difficulties associated with the transport and storage of synthesis gas, it is typically generated in situ. Thus, a significant expense for new methyl acetate and methanol production capacity is the capital and operating costs associated with synthesis gas generation.

SUMMARY OF THE INVENTION

It has now been found that the above-described problems may be overcome or at least mitigated by integrating a process for the production of methyl acetate by the carbonylation of dimethyl ether with a methanol synthesis process; which integrated process uses a synthesis gas feed to the carbonylation reaction without the need for an additional synthesis gas feed for methanol synthesis and wherein methyl acetate is removed from synthesis gas streams prior to their use in methanol synthesis.

Accordingly, the present invention provides an integrated process for the production of methyl acetate and methanol which process comprises:

(i) feeding synthesis gas and dimethyl ether into a carbonylation reaction zone and reacting therein the synthesis gas and dimethyl ether in the presence of a carbonylation catalyst to form a gaseous carbonylation reaction product comprising methyl acetate and synthesis gas enriched in hydrogen;

(ii) withdrawing carbonylation reaction product from the carbonylation reaction zone and recovering therefrom a methyl acetate-rich liquid stream and a synthesis gas stream comprising residual amounts of methyl acetate;

(iii) scrubbing in a scrubbing zone at least a portion of the synthesis gas recovered from the carbonylation reaction product with a liquid scrubbing solvent to reduce the content of the methyl acetate in the synthesis gas and to obtain a scrubbed synthesis gas depleted in methyl acetate and a liquid solvent stream comprising methyl acetate;

(iv) passing scrubbed synthesis gas to a methanol synthesis zone and contacting it therein with a methanol synthesis catalyst to form a methanol synthesis product comprising methanol and unconverted synthesis gas.

Advantageously, the present invention provides a process for the production of both methyl acetate and methanol from synthesis gas whilst minimizing loss of valuable carbon monoxide feedstock from methyl acetate production. Unreacted carbon monoxide and hydrogen present in a carbonylation reaction stream is usefully converted to methanol in the methanol synthesis zone thereby eliminating the need for any additional source of synthesis gas for methanol synthesis.

Advantageously, the present invention provides a process which allows for the reduction or complete elimination of the need to dispose of purge gas vented from a process for the carbonylation of dimethyl ether with carbon monoxide in the presence of a catalyst to produce methyl acetate, thereby reducing the loss of valuable components such as dimethyl ether, carbon monoxide and methyl acetate.

Advantageously, the present invention provides a process which reduces by-product formation during methanol synthesis by the substantial removal of methyl acetate from feeds to methanol synthesis, thereby mitigating an undesirable loss in methanol productivity.

Desirably, the present invention allows methanol to be produced from a synthesis gas feed which has a stoichiometric number which is sub-optimal for methanol production whilst also allowing the production of methyl acetate.

Furthermore, the present invention allows the production of methanol whilst avoiding or mitigating the need for imported carbon dioxide thereby reducing methanol process costs.

BRIEF DESCRIPTION OF THE DRAWINGS

The accompanying drawings, which are incorporated in and constitute part of the specification, illustrate embodiments of the invention and, together with the description, serve to explain the features, advantages, and principles of the invention. In the drawings.

DETAILED DESCRIPTION OF THE INVENTION

As discussed above, synthesis gas comprises carbon monoxide and hydrogen. Optionally, synthesis gas may also comprise carbon dioxide. Typically, synthesis gas may also comprise small amounts of inert gases such as nitrogen and methane and water vapour. Conventional processes for converting hydrocarbon sources to synthesis gas include steam reforming and partial oxidation. Examples of hydrocarbon sources used in synthesis gas production include bio-mass, natural gas, methane, $C_2$-$C_5$ hydrocarbons, naphtha, coal and heavy petroleum oils.

Steam reforming generally comprises contacting a hydrocarbon with steam to form synthesis gas. The process preferably includes the use of a catalyst, such as those based on nickel.

Partial oxidation generally comprises contacting a hydrocarbon with oxygen or an oxygen-containing gas such as air to form synthesis gas. Partial oxidation takes place with or without the use of a catalyst, such as those based on rhodium, platinum or palladium.

In the present invention, synthesis gas comprising carbon monoxide and hydrogen is contacted in a carbonylation reaction zone with a suitable carbonylation catalyst to produce a gaseous carbonylation reaction product comprising methyl acetate and a synthesis gas enriched in hydrogen.

Suitably, the synthesis gas feed to the carbonylation reaction zone is synthesis gas generated by the steam reforming of hydrocarbons or by the partial oxidation of hydrocarbons. Preferably the synthesis gas is generated by the partial oxidation of natural gas or methane.

Suitably, the synthesis gas formed in the synthesis gas generating process is cooled prior to use in the carbonylation reaction. Preferably, the synthesis gas is cooled so as to condense at least a portion of the water vapour formed during the synthesis gas forming process.

Synthesis gas supplied to the carbonylation reaction zone is preferably a dry synthesis gas. Water may be removed from synthesis gas, using any suitable means, for example a molecular sieve.

The synthesis gas feed to the carbonylation reaction zone comprises fresh synthesis gas. For the present purposes, fresh synthesis gas includes stored sources of synthesis gas. Suitably, the synthesis gas feed consists essentially of fresh synthesis gas, that is in the absence of recycle synthesis gas.

Suitably, the fresh synthesis gas feed to the carbonylation reaction zone comprises carbon dioxide. Carbon dioxide may be present in the synthesis gas feed in an amount of not greater than 50 mol %, such as in the range 0.5 to 12 mol %.

The stoichiometric number (SN) of a fresh synthesis gas is not critical and may vary significantly. Desirably, to provide a suitable synthesis gas composition to the methanol synthesis zone for the stoichiometrically balanced production of methanol, the fresh synthesis gas contains at least a partial excess of hydrogen compared to carbon monoxide and carbon dioxide. Suitably, therefore a fresh synthesis gas has a stoichiometric number in the range 0.9 to 1.3, preferably in the range 1.0 to 1.2, such as 1.0 to 1.1. Suitably, the fresh synthesis gas has a stoichiometric number which is lower than the stoichiometric number of the scrubbed synthesis gas passed to the methanol synthesis zone.

Preferably, the synthesis gas feed to the carbonylation reaction zone further comprises recycle synthesis gas. Suitable sources of recycle synthesis gas include synthesis gas recovered from the carbonylation reaction product.

Preferably, in the present invention, the synthesis gas feed to the carbonylation reaction zone comprises a mixture of fresh synthesis gas and synthesis gas recovered from the carbonylation reaction product.

The recycle synthesis gas, such as that recovered from the carbonylation reaction product may also comprise carbon dioxide. Where carbon dioxide is present in a synthesis gas feed comprising fresh and recycle synthesis gas, it is preferably present in a total amount of not greater than 50 mol %, such as in the range 0.5 to 12 mol %.

Synthesis gas may be fed to the carbonylation reaction zone as one or more streams. The one or more streams may be either fresh synthesis gas or a mixture of fresh and recycle synthesis gas.

Preferably, prior to use in the carbonylation reaction, the synthesis gas, whether fresh, recycle or combinations thereof, is heated, for example in one or more heat exchangers, to the desired carbonylation reaction temperature.

The carbon monoxide partial pressure in the carbonylation reaction zone should be sufficient to permit the production of methyl acetate. Thus, suitably, the carbon monoxide partial pressure is in the range 0.1 to 100 barg (10 kPa to 10,000 kPa), such as 10 to 65 barg (1000 kPa to 6500 kPa).

The hydrogen partial pressure in the carbonylation reaction zone is suitably in the range 1 barg to 100 barg (100 KPa to 10,000 kPa), preferably 10 to 75 barg (1000 kPa to 7500 kPa).

The dimethyl ether feed to the carbonylation reaction zone may be fresh dimethyl ether or a mixture of fresh and recycle dimethyl ether. Suitably, recycle streams comprising dimethyl ether may be obtained from any part of the process downstream of the carbonylation reaction including, for example, synthesis gas streams recovered from the carbonylation reaction product.

Dimethyl ether may be fed to the carbonylation reaction zone as one or more fresh dimethyl ether streams or as one or more streams comprising a mixture of fresh and recycle dimethyl ether.

Dimethyl ether and synthesis gas may be fed to the carbonylation reaction zone as one or more separate streams but preferably are supplied as one or more combined synthesis gas and dimethyl ether streams.

In an embodiment, the dimethyl ether and synthesis gas are fed to the carbonylation reaction zone as a combined stream which combined stream is heated to the desired carbonylation reaction temperature, for example in one or more heat exchangers, prior to use in the carbonylation reaction.

In commercial practice, dimethyl ether is produced by the catalytic conversion of methanol over methanol dehydration catalysts. This catalytic conversion results in a product which is predominantly dimethyl ether but it may also contain low levels of methanol and/or water. The presence of significant amounts of water in a zeolite catalysed carbonylation of dimethyl ether tends to inhibit the production of methyl acetate product. In addition, water may be generated in the carbonylation reaction via side-reactions. Dimethyl ether for use in the carbonylation reaction of the present invention may contain small amounts of one or more of water and methanol provided that the total amount of methanol and water is not so great as to significantly inhibit the production of methyl acetate. Suitably, the dimethyl ether (including recycles) may contain water and methanol in a total amount in the range 1 ppm to 10 mol %, for example 1 ppm to 2 mol %, such as 1 ppm to 1 mol %, preferably in the range from 1 ppm to 0.5 mol %.

Preferably, the dimethyl ether (fresh and recycle) is dried before use in the carbonylation reaction.

The concentration of dimethyl ether may be in the range of 1 mol % to 20 mol %, suitably in the range 1.5 mol % to 15 mol %, for instance 5 to 15 mol %, for example 2.5 to 12 mol %, such as 2.5 to 7.5 mol % based on the total of all streams to the carbonylation reaction zone.

The molar ratio of carbon monoxide to dimethyl ether in the carbonylation reaction zone is suitably in the range 1:1 to 99:1, for example 1:1 to 25:1, such as 2:1 to 25:1.

Carbon dioxide reacts with hydrogen to form water and carbon monoxide. This reaction is commonly referred to as the reverse water gas shift reaction. Thus, where it is desired to utilise synthesis gas comprising carbon dioxide, to mitigate the effect of water on the carbonylation reaction, it is preferred that the carbonylation catalyst is not active for the reverse water-gas shift reaction or for the production of methanol. Preferably, the carbonylation catalyst comprises an aluminosilicate zeolite.

Zeolites comprise a system of channels which may be interconnected with other channel systems or cavities such as side-pockets or cages. The channel systems are defined by ring structures which rings may comprise, for example, 8, 10, or 12 members. Information about zeolites, their framework structure types and channel systems is published in the Atlas of Zeolite Framework Types, C. H. Baerlocher, L. B. Mccusker and D. H. Olson, 6th Revised Edition, Elsevier, Amsterdam, 2007 and is also available on the website of the International Zeolite Association at www.iza-online.org.

Suitably, the carbonylation catalyst is an aluminosilicate zeolite which comprises at least one channel which is defined by an 8-member ring. The aperture of the zeolite channel system defined by the 8-membered ring should be of such dimensions that the reactant dimethyl ether and carbon monoxide molecules can diffuse freely in and out of the zeolite framework. Suitably, the aperture of the 8-member ring channel of the zeolite has dimensions of at least 2.5×3.6 Angstroms. Preferably, the channel defined by the 8-member ring is interconnected with at least one channel defined by a ring with 10 or 12 members.

Non-limiting examples of aluminosilicate zeolites which comprise at least one channel which is defined by an 8-membered ring include zeolites of framework structure type MOR (for example, mordenite), FER (for example, ferrierite), OFF (for example, offretite) and GME (for example, gmelinite).

A preferred carbonylation catalyst is a mordenite zeolite.

The carbonylation catalyst may be a zeolite in its hydrogen form. Preferably, the carbonylation catalyst is mordenite in its hydrogen form.

The carbonylation catalyst may be a zeolite which is fully or partially loaded with one or more metals. Suitable metals for loading onto the zeolite include copper, silver, nickel, iridium, rhodium, platinum, palladium or cobalt and combinations thereof, preferably copper, silver and combinations thereof. The metal loaded form may be prepared by techniques such as ion-exchange and impregnation. These techniques are well-known and typically involve exchanging the hydrogen or hydrogen precursor cations (such as ammonium cations) of a zeolite with metal cations.

The carbonylation catalyst may be an aluminosilicate zeolite which, in addition to aluminium and silicon, has present in its framework one or more additional metals such as trivalent metals selected from at least one of gallium, boron and iron. Suitably, the carbonylation catalyst may be a zeolite which contains gallium as a framework element. More suitably, the carbonylation catalyst is a mordenite which contains gallium as a framework element, most suitably the carbonylation catalyst is a mordenite which contains gallium as a framework element and is in its hydrogen form.

The carbonylation catalyst may be a zeolite which is composited with at least one binder material. As will be appreciated by those of ordinary skilled in the art, binder materials are selected such that the catalyst is suitably active and robust under the carbonylation reaction conditions. Examples of suitable binder materials include inorganic oxides, such as silicas, aluminas, alumina-silicates, magnesium silicates, magnesium aluminium silicates, titanias and zirconias. Preferred binder materials include aluminas, alumina-silicates and silicas, for example, boehemite type alumina.

The relative proportions of the zeolite and the binder material may vary widely but suitably, the binder material may be present in a composite in an amount in the range of 10% to 90% by weight of the composite, preferably, in the range of 10% to 65% by weight of the composite.

Zeolite powders may also be formed into particles without the use of a binder. Typical zeolite catalyst particles include extrudates whose cross sections are circular or embrace a plurality of arcuate lobes extending outwardly from the central portion of the catalyst particles.

In an embodiment of the present invention, the carbonylation catalyst is a zeolite, such as a mordenite which is composited with at least one inorganic oxide binder material, which may suitably be selected from aluminas, silicas and alumina-silicates, and is utilised in the form of a shaped body, such as an extrudate. In particular, the carbonylation catalyst is a mordenite composited with an alumina, such as a boehmite alumina. The mordenite composited with the alumina may contain gallium as a framework element.

The silica to alumina molar ratio of the zeolites for use as carbonylation catalysts in the present invention is the bulk or overall ratio. This can be determined by any one of a number of chemical analysis techniques. Such techniques include x-ray fluorescence, atomic absorption and ICP (inductive coupled plasma). All will provide substantially the same silica to alumina molar ratio value.

The bulk silica to alumina molar ratio (herein also termed "SAR") of synthetic zeolites will vary. For example, the SAR of a zeolite, such as mordenite, may range from as low as 5 to over 90.

The SAR of a zeolite for use as a carbonylation catalyst in the present invention may suitably be in the range from 10:1 to 90:1, for example 20:1 to 60:1.

It is preferred that a zeolite carbonylation catalyst is activated immediately before use, typically by heating it at elevated temperature for at least one hour under flowing nitrogen, carbon monoxide, hydrogen or mixtures thereof.

Preferably, the carbonylation reaction is carried out under substantially anhydrous conditions. Suitably therefore, as discussed above, to limit the presence of water in the carbonylation reaction, all reactants, including fresh synthesis gas, fresh dimethyl ether, any recycles thereof and the catalyst are dried prior to use in the carbonylation reaction. Suitably, the combined amount of water and methanol (a source of water) present in the carbonylation reaction zone is limited to be in the range 1 ppm to 0.5 mol %, preferably in the range 1 ppm to 0.1 mol %, and most preferably in the range 1 ppm to 0.05 mol %. Desirably, the combined amount of water and methanol introduced into the carbonylation reaction zone is not more than 0.5 mol %, for example 0 to 0.5 mol %, such as 1 ppm to 0.5 mol %.

The carbonylation catalyst may be employed in a fixed bed carbonylation reaction zone, for example in the shape of pipes or tubes, where the dimethyl ether and synthesis gas feeds, typically in gaseous form are passed over or through the carbonylation catalyst.

The carbonylation reaction is carried out in the vapour phase.

The synthesis gas and dimethyl ether are reacted in the presence of the carbonylation catalyst under reaction conditions effective to form a gaseous carbonylation reaction product comprising methyl acetate.

Preferably, the carbonylation reaction is carried out at a temperature in the range of 100° C. to 350° C., for example in the range 250° C. to 350° C.

Preferably, the carbonylation reaction is carried out at a total pressure in the range 1 to 200 barg (100 kPa to 20,000 kPa), for example 10 to 100 barg (1000 kPa to 10,000 kPa), such as 50 to 100 barg (5000 kPa to 10,000 kPa).

In an embodiment, the carbonylation reaction is carried out at temperatures in the range 250° C. to 350° C. and at total pressures in the range 50 to 100 barg (5000 kPa to 10,000 kPa).

In a preferred embodiment, synthesis gas and dimethyl ether, preferably containing water and methanol in no more than a combined amount in the range 1 ppm to 10 mol %, are reacted in the presence of a carbonylation catalyst, such as an aluminosilicate zeolite having at least one channel which is defined by an 8-membered ring, for example mordenite, preferably mordenite in its hydrogen form, at a temperature in the range 100° C. to 350° C. and at a total pressure in the range 10 to 100 barg (1000 kPa to 10,000 kPa) to form a gaseous carbonylation reaction product comprising methyl acetate and synthesis gas enriched in hydrogen.

Dimethyl ether and fresh synthesis gas (optionally comprising carbon dioxide and any recycles) may suitably be fed to the carbonylation reaction zone at a total gas hourly space velocity of flow of gas through the catalyst bed (GHSV) is in the range 500 to 40,000 h$^{-1}$, such as 2000 to 20,000 h$^{-1}$.

Preferably, the carbonylation reaction is carried out substantially in the absence of halides, such as iodide. By the term 'substantially' is meant that the halide, for example the total iodide, content of the feed streams to the carbonylation reaction zone is less than 500 ppm, preferably less than 100 ppm.

Hydrogen present in synthesis gas is essentially inactive in the carbonylation reaction and thus the hydrogen content of synthesis gas withdrawn from the carbonylation reaction zone is enriched relative to the hydrogen content of the synthesis gas feed to the carbonylation reaction zone.

The carbonylation reaction product withdrawn from the carbonylation reaction zone comprises methyl acetate and synthesis gas enriched in hydrogen. Additional components which typically may be present in the carbonylation reaction product include one or more of unreacted dimethyl ether, and small amounts of water, acetic acid and methanol.

Carbon dioxide is generally unconsumed in the carbonylation reaction, thus when the synthesis gas feed to the carbonylation reaction zone comprises carbon dioxide, the carbonylation reaction product will also comprise carbon dioxide.

Carbonylation reaction product is withdrawn from the carbonylation reaction zone in gaseous form.

A methyl acetate-rich liquid stream and a synthesis gas stream comprising residual amounts of methyl acetate are recovered from the carbonylation reaction product.

Suitably, the carbonylation reaction product is withdrawn from the carbonylation reaction zone, cooled and separated to recover a methyl acetate-rich liquid stream and a synthesis gas stream.

The cooling of the carbonylation reaction product may be carried out using one or more heat exchange means, such as conventional heat exchangers, to cool the carbonylation reaction product to, for example a temperature in the range of 50° C. or less, suitably to a temperature in the range 40° C. to 50° C. The cooled carbonylation reaction product may be separated, for example in one or more gas/liquid separation means, such as a knock-out drum or a tangential inlet drum, to recover a methyl acetate-rich liquid stream and a synthesis gas stream. The methyl acetate-rich liquid stream will comprise mainly methyl acetate and may also comprise additional components selected from one or more of unreacted dimethyl ether, methanol, water, acetic acid and dissolved synthesis gas.

Residual amounts of methyl acetate may be retained in the synthesis gas stream. The amount of methyl acetate present in the synthesis gas can vary but, typically, the synthesis gas comprises methyl acetate in an amount in the range 0.1 to 5 mol %, for example 0.5 to 5 mol %, such as 0.5 to 2 mol %, for instance 0.5 to 1 mol %. The synthesis gas stream may also comprise small amounts of additional components, typically, one or more of unreacted dimethyl ether, carbon dioxide and acetic acid.

Methyl acetate may be recovered from the methyl acetate-rich liquid stream, for example by distillation, and sold as such or used as a feedstock in downstream chemical processes.

In an embodiment of the present invention, methyl acetate is recovered from at least a portion of the methyl acetate-rich liquid stream and the recovered methyl acetate is converted to acetic acid, preferably by a hydrolysis process. Hydrolysis of the recovered methyl acetate may be carried out using known processes, such as catalytic distillation processes. Typically, in catalytic distillation processes for the hydrolysis of methyl acetate, methyl acetate is hydrolysed with water in a fixed-bed reactor employing an acidic catalyst, such as an acidic ion exchange resin or a zeolite, to produce a mixture comprising acetic acid and methanol from which acetic acid and methanol may be separated by distillation, in one or more distillation stages.

It has now been found that the presence of methyl acetate in synthesis gas feeds to methanol synthesis is highly undesirable as its presence can lead to the formation of unwanted by-products such as one or more of ethanol and acetic acid resulting in a loss of catalytic performance and/or methanol productivity.

Thus, in the present invention, at least a portion of the synthesis gas recovered from the carbonylation reaction product is scrubbed with a liquid scrubbing solvent to reduce the methyl acetate content of the synthesis gas. If desired, all of the synthesis gas may be scrubbed. However, preferably, a portion of the synthesis gas recovered from the carbonylation reaction product is recycled to the carbonylation reaction zone.

Suitably, the synthesis gas recovered from the carbonylation reaction product is split into at least two portions, wherein a first portion of the synthesis gas recovered from the carbonylation reaction product is scrubbed and at least one other portion which, for example equal to the first portion, is recycled to the carbonylation reaction zone. Preferably, however, the synthesis gas recovered from the carbonylation reaction product is split into a major portion and a minor portion. More preferably, the synthesis gas is split into a major portion and a minor portion, wherein the major portion is recycled to the carbonylation reaction zone and the minor portion is scrubbed.

Suitably, the major portion is at least 50 mol % of the synthesis gas, such as in the range 60 to 85 mol %, for example 70 to 80 mol %. Suitably, the minor portion is less than 50 mol %, such as in the range 10 to 30 mol %, for example 20 to 30 mol %.

In one embodiment, 70 to 80 mol % of the synthesis gas is recycled to the carbonylation reaction zone and 20 to 30 mol % of the synthesis gas is scrubbed.

Suitably, the synthesis gas may be compressed, in one or more compressors, prior to recycle to the carbonylation reaction zone.

If desired, a portion of the synthesis gas recovered from the carbonylation reaction product can be vented as purge gas but, preferably, substantially all of the recovered synthesis gas is scrubbed or is recycled to the carbonylation reaction or a combination of both.

Scrubbing of the synthesis gas to reduce the methyl acetate content thereof is conducted in a scrubbing zone. A scrubbing zone may contain one or more scrubbing units, suitably of conventional design, for example a column or tower within which high surface area materials, such as trays or packing, is arranged so as to enable intimate contact of the synthesis gas and the scrubbing solvent and to ensure good mass transfer between the gas and liquid phases. Desirably, the scrubbing is performed by counter-current contact of the synthesis gas and the scrubbing solvent so that the synthesis gas will flow upwardly through the column or tower and the scrubbing solvent will flow downwardly through the column or tower.

Suitably, a liquid stream comprising the scrubbing solvent and methyl acetate is withdrawn from the lower portion of a scrubbing unit.

Suitably, synthesis gas depleted in methyl acetate content is removed from the upper portion of a scrubbing unit.

Synthesis gas to be scrubbed may be subjected to multiple scrubbing treatments. Each scrubbing may be conducted with the same or different scrubbing solvent.

Where the synthesis gas is subjected to more than one scrubbing treatment, such as two scrubbing treatments, the synthesis gas may be subjected to a first scrubbing by contacting the synthesis gas with a first scrubbing solvent to obtain a liquid solvent stream comprising methyl acetate and synthesis gas depleted in methyl acetate. The synthesis gas depleted in methyl acetate is subjected to a second scrubbing by contacting the synthesis gas depleted in methyl acetate with a second liquid scrubbing solvent to obtain a liquid solvent stream comprising methyl acetate, and synthesis gas further depleted in methyl acetate.

Multiple scrubbing of the synthesis gas may, and generally does, result in the liquid solvent streams from each scrubbing having a different composition. For example where the scrubbing solvent comprises methanol, most of the methyl acetate present in the synthesis gas to be scrubbed will be absorbed by the scrubbing solvent in the first scrubbing treatment, such that the liquid methanol stream from the first scrubbing will contain higher amounts of methyl acetate than liquid methanol streams obtained from subsequent scrubbing treatments.

Liquid solvent streams from a first and any subsequent scrubbing may be combined to form a single liquid stream.

Preferably, the temperature of a scrubbing solvent on entry into the scrubbing zone is from −50° C. to 100° C., more preferably from 0° C. to 60° C., most preferably from 35° C. to 55° C.

The scrubbing solvent may be any solvent capable of absorbing methyl acetate. Preferably, the scrubbing solvent comprises methanol. The scrubbing solvent may be pure methanol. Alternatively, the scrubbing solvent may comprise a mixture of methanol and other components, such as a mixture of methanol and one or more of water and dimethyl ether. Mixtures of methanol and one or more of dimethyl ether and water for use as the scrubbing solvent may be obtained from the methanol synthesis product produced in the methanol synthesis reaction.

Suitably, the scrubbing solvent is selected from imported methanol, a methanol-rich stream recovered from the methanol synthesis product and mixtures thereof.

Suitably, all or a portion of a methanol-rich stream recovered from the methanol synthesis product is used as a scrubbing solvent.

Preferably, a scrubbing solvent which comprises a mixture of methanol and water contains water in an amount of less than 20 w/w %, more preferably less than 10 w/w %, and most preferably less than 5 w/w %.

Preferably, a scrubbing solvent which comprises a mixture of methanol and dimethyl ether contains dimethyl ether in an amount of less than 20 w/w %, more preferably less than 10 w/w %.

In some or all embodiments of the present invention, at least a portion of the synthesis gas recovered from the carbonylation reaction product is subjected to multiple scrubbing treatments, such as two or more scrubbing treatments, in one scrubbing unit with a liquid scrubbing solvent. Suitably, the liquid solvent employed in each scrubbing treatment comprises, and preferably consists of, a portion of the methanol-rich stream recovered from the methanol synthesis product.

Dimethyl ether and acetic acid which may be present in synthesis gas recovered from the carbonylation reaction product are generally absorbed by methanol-containing scrubbing solvents and consequently these components are removed, together with methyl acetate, as part of the liquid methanol solvent stream.

The liquid solvent stream comprising absorbed methyl acetate may be subjected to processing and/or purification steps to recover the scrubbing solvent therefrom.

It is preferred to remove at least 80%, preferably at least 90%, more preferably at least 95% and most preferably at least 99%, of the methyl acetate from the synthesis gas.

Suitably, synthesis gas supplied to the methanol synthesis zone comprises methyl acetate in an amount 0 to 1 mol %, such as 0 to less than 1 mol %.

Scrubbing of the synthesis gas does not substantially alter the amounts of carbon monoxide, hydrogen and carbon dioxide contained therein. However, if one or more of carbon monoxide, hydrogen and carbon dioxide are present in the scrubbing solvent a portion of any such components may be released from the scrubbing solvent and form part of the scrubbed synthesis gas. In general however, the stoichiometric number of the scrubbed synthesis gas corresponds approximately to the stoichiometric number of the synthesis gas recovered from the carbonylation reaction product.

The stoichiometric number of the synthesis gas recovered from the carbonylation reaction product will depend principally upon the stoichiometric number of fresh synthesis gas used in the carbonylation reaction and the degree of conversion therein, but it may be adjusted by varying the amount of synthesis gas which is recovered from the carbonylation reaction product and recycled to the carbonylation reaction zone. The stoichiometric number of the scrubbed synthesis gas may therefore be adjusted so as to be optimal for methanol synthesis by altering one or more of these factors, that is, in the range 1.5 to 2.5, preferably in the range 2.0 to 2.1, more preferably 2.05.

Scrubbed synthesis gas depleted in methyl acetate can be directly passed to a methanol synthesis zone. At least a portion of the scrubbed synthesis gas is passed to the methanol synthesis zone for the production of methanol. If desired, the scrubbed synthesis gas in its entirety may be passed to the methanol synthesis zone.

The methanol synthesis process used to manufacture the methanol synthesis product of the present invention can be any suitable process. Commercially, methanol is produced by the catalytic conversion of carbon monoxide and hydrogen according to the overall equation $CO+2H_2 \leftrightarrows CH_3OH$. The reaction proceeds in accordance with the following reactions:

$$CO_2 + 3H_2 \leftrightarrows CH_3OH + H_2O \quad (I)$$

$$H_2O + CO \leftrightarrows CO_2 + H_2 \quad (II)$$

Conventionally, the carbon monoxide and hydrogen required for methanol production is obtained from synthesis gas supplied directly to a methanol synthesis zone from reforming or partial oxidation processes. Advantageously, in the present invention, there may be utilised a single synthesis gas feed to enable the production of both methyl acetate and methanol. In the present invention it is not necessary to supply fresh synthesis gas for methanol synthesis in addition to the synthesis gas supplied for use in the carbonylation reaction. As described above, carbon monoxide and hydrogen required for the methanol synthesis is obtained from the synthesis gas recovered from the carbonylation reaction product.

In a preferred embodiment, the process of the present invention further comprises the steps of:

(v) withdrawing methanol synthesis product from the methanol synthesis zone and recovering therefrom a methanol-rich liquid stream and a synthesis gas stream; and (vi) recycling at least a portion of the synthesis gas stream recovered from the methanol synthesis product to the methanol synthesis zone.

Scrubbed synthesis gas passed to the methanol synthesis zone may be employed as the sole source of synthesis gas for methanol synthesis. Preferably, however, the scrubbed synthesis gas is passed to the methanol synthesis zone as a combined feed with at least a portion of synthesis gas recovered from the methanol synthesis product. Preferably, the scrubbed synthesis gas is combined with at least a portion of synthesis gas recovered from the methanol synthesis product so that the combined synthesis gas passed to the methanol synthesis zone is adjusted for the approximately stoichiometric production of methanol. Suitably, the scrubbed synthesis gas has a stoichiometric number in the range 1.5 to 2.5, preferably in the range 2.01 to 2.1, more preferably 2.05.

Prior to use in the methanol synthesis zone, the synthesis gas feeds to the methanol synthesis zone, such as the scrubbed synthesis gas and a combined feed of scrubbed synthesis gas and synthesis gas recovered from the methanol synthesis product, may be heated, for example in one or more heat exchangers, to the desired methanol synthesis temperature.

In order for the methanol synthesis to proceed favourably, the synthesis gas recovered from the methanol synthesis product, or a combined feed of synthesis gas recovered from the methanol synthesis product and scrubbed synthesis gas, is preferably compressed to the desired methanol synthesis pressure.

The synthesis of methanol requires a source of carbon dioxide. Sources of carbon dioxide include synthesis gas, carbon dioxide generated in-situ during methanol synthesis and imported carbon dioxide. Carbon dioxide can be generated in-situ from water formed in the methanol synthesis process and by the addition of water to the methanol synthesis. However, there are a number of disadvantages associated with the addition of water to the methanol synthesis for in-situ generation of carbon dioxide, including the requirements for additional processing and the provision of a suitable source of water. However, if desired, at least one of water and imported carbon dioxide may be introduced into the methanol synthesis zone. Most desirably, however, all of the carbon dioxide required for methanol synthesis is derived from the synthesis gas feed to the carbonylation reaction or from in-situ generation from water formed in the methanol synthesis process.

Carbon dioxide which is unconsumed in the methanol synthesis is withdrawn from the methanol synthesis zone as part of the methanol synthesis product. If desired, carbon dioxide may be recovered from the methanol synthesis product, for example by conventional liquid/gas separation techniques.

In general, dimethyl ether does not take part in methanol synthesis and consequently, dimethyl ether which may be present in the synthesis gas passed to the methanol synthesis zone is withdrawn from the methanol synthesis zone as part of the methanol synthesis product.

The methanol synthesis is accomplished in the presence of a methanol synthesis catalyst. At least a portion of the scrubbed synthesis gas, and optionally at least a portion of synthesis gas recovered from the methanol synthesis product, is contacted in the methanol synthesis zone with a methanol synthesis catalyst.

A number of catalysts active for methanol synthesis are known in the art and are also available commercially, for example, the commercial Katalco™ methanol synthesis catalysts available from Johnson Matthey plc. Typically the catalysts are based on copper and may also contain one or more additional metals such as zinc, magnesium and aluminium.

In one embodiment of this invention, the methanol synthesis catalyst comprises copper, zinc oxide and alumina.

The methanol synthesis catalyst may be employed in a fixed bed methanol synthesis zone, for example in the shape of pipes or tubes, where the scrubbed synthesis gas stream and optionally synthesis gas recovered from the methanol synthesis product are passed over or through the methanol synthesis catalyst.

Preferably, the methanol synthesis is carried out in the vapour phase.

Synthesis gas is contacted with the methanol synthesis catalyst under reactions conditions effective to effect the conversion of synthesis gas to form a methanol synthesis product comprising methanol and unconverted synthesis gas.

Suitably, methanol synthesis is carried out at a temperature of from 210° C. to 300° C., such as in the range 210° C. to 270° C. or 220° C. to 300° C., for example in the range 230° C. to 275° C.

Preferably, the methanol synthesis is carried out at a total pressure in the range 25 to 150 barg (2500 kPa to 15,000 kPa), for example in the range 50 to 100 barg (5000 kPa to 10,000 kPa).

Suitably, the methanol synthesis is carried out at a temperature in the range in the range 230° C. to 275° C. and at a total pressure in the range 50 to 100 barg (5000 kPa to 10,000 kPa).

In an embodiment of the present invention, methanol synthesis is carried out at a temperature of from 210° C. to 270° C. and at a total pressure in the range 50 to 100 barg (5000 kPa to 10,000 kPa).

In a preferred embodiment, at least a portion of the scrubbed synthesis gas, optionally combined with at least a portion of the synthesis gas recovered from the methanol synthesis product, is contacted with a methanol synthesis catalyst based on copper, preferably a catalyst comprising copper, zinc and aluminium, at a temperature in the range 220° C. to 300° C. or in the range 210° C. to 270° C. and at a total pressure in the range 25 to 150 barg (2500 kPa to 15,000 kPa).

Suitably, the total gas hourly space velocity of the total feed to the methanol synthesis zone (including any recycle synthesis gas, water and any imported carbon dioxide) is in the range 500 to 40,000 h$^{-1}$.

Contacting of the scrubbed synthesis gas, optionally combined with at least a portion of the synthesis gas recovered from the methanol synthesis product, with the methanol synthesis catalyst produces a crude methanol synthesis product comprising methanol and unconverted synthesis gas. Depending on the exact nature of the components present in the synthesis gas feed(s) for methanol synthesis, the methanol synthesis product may further comprise, in addition to methanol and unconverted synthesis gas, additional components, such as one or more of carbon dioxide, water and dimethyl ether.

The methanol synthesis product is withdrawn from the methanol synthesis zone, preferably in vapour form.

Methanol may be recovered from the withdrawn methanol synthesis product by known recovery techniques. Suitably, methanol may be recovered from at least a portion of the methanol synthesis product, for example by reducing the temperature of the methanol synthesis product to generate a cooled methanol-synthesis gas mixture. Suitably, the temperature of the mixture is reduced to a temperature in the range 30° C. to 50° C., preferably in the range 35° C. to 45° C. The cooled methanol-synthesis gas mixture is separated to recover a methanol-rich liquid stream and a synthesis gas stream.

Preferably, substantially all of the methanol synthesis product is separated to recover a methanol-rich liquid stream and a synthesis gas stream.

Separation of at least a portion of the methanol synthesis product may be carried out in one or more separation units. Each of the separation unit(s) may be of conventional design and may comprise one or more heat exchange means to cool the methanol synthesis product to condense out liquid methanol together with other condensable components such as water, from the methanol synthesis product and one or more gas/liquid separation means, such as a knock-out drum or a tangential inlet drum, to separate the cooled methanol-synthesis gas mixture to recover a methanol-rich liquid stream and a synthesis gas stream.

Alternatively, separation of the methanol synthesis product may be carried out directly in the methanol synthesis zone, that is, by withdrawing from the methanol synthesis zone one or more gaseous streams comprising synthesis gas and one or more liquid streams rich in methanol.

The methanol-rich liquid stream may comprise small amounts of water and unreacted dimethyl ether.

The methanol-rich liquid stream is suitable for use as the scrubbing solvent. Thus, preferably, in the present invention, at least a portion of, such as substantially all of the methanol-rich liquid stream is used as the scrubbing solvent. Advantageously, this avoids the need to import methanol or any other suitable solvent for use as the scrubbing solvent.

Where multiple scrubbing treatments are conducted, the methanol-rich liquid stream supplied to the scrubbing zone may be divided and equal or unequal portions of the stream supplied to each of two or more scrubbing units in the scrubbing zone. For example, a minor portion of the methanol-rich liquid stream, such as >0% to 20%, is supplied to a first scrubbing unit and a major portion of the stream, such as 80% to <100%, is supplied to a second scrubbing unit.

Methanol may be recovered from one or more of the methanol synthesis product withdrawn from the methanol synthesis zone, the methanol-rich liquid stream recovered from the methanol synthesis product and liquid solvent streams comprising methanol obtained from the scrubbing of the synthesis gas, by any conventional purification means, such as distillation, and sold as such, or the methanol may be used, for example, as a feedstock in a variety of chemical processes. For example, methanol may be carbonylated with carbon monoxide in the presence of a Group VIII noble metal catalyst, such as rhodium, iridium or mixtures thereof, to form acetic acid.

Alternatively, the methanol may be dehydrated in the presence of a suitable catalyst to form dimethyl ether. Suitable catalysts include aluminas, such as gamma-alumina.

Dimethyl ether which may be present in the methanol-rich liquid stream may be recovered therefrom, for example by distillation. The recovered dimethyl ether may be recycled to the carbonylation reaction zone.

Synthesis gas recovered from the methanol synthesis product may comprise carbon dioxide.

At least a portion of the synthesis gas recovered from the methanol synthesis product may be recycled to the methanol synthesis zone. Suitably, 90% to 99% of the synthesis gas may be recycled to the methanol synthesis zone.

If desired, to reduce the build-up of inert gases in the methanol synthesis zone, a portion of the synthesis gas recovered from the methanol synthesis product may be vented as a purge stream. Suitably, 1 to 10% of the synthesis gas recovered from the methanol synthesis product may be vented as a purge stream.

Suitably, in each of the carbonylation reaction zone and the methanol synthesis zone, the reaction is conducted as a heterogeneous vapour phase reaction.

The integrated process of the present invention and its component methyl acetate and methanol production processes may each be operated as a continuous process or as a batch process preferably, the integrated process is operated as a continuous process.

Figure 1:
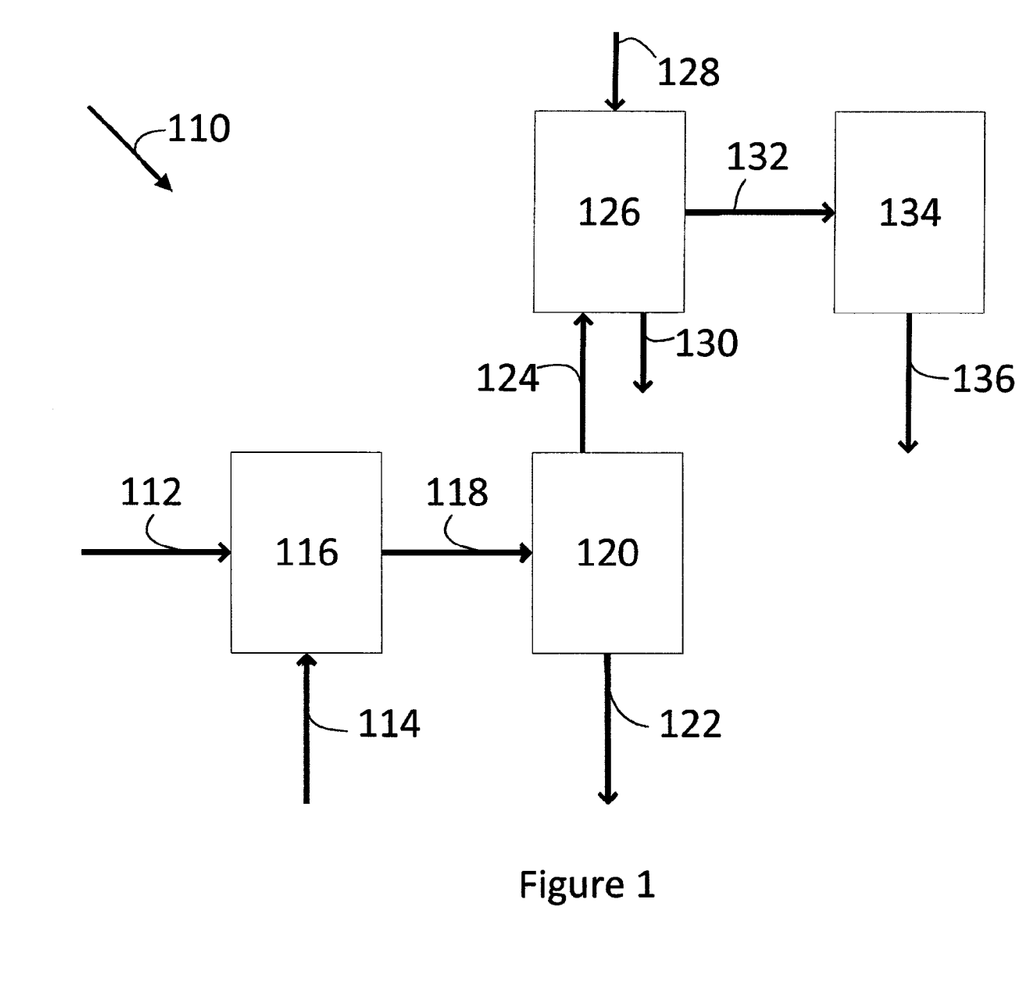
FIG. 1 is a block diagram showing one embodiment of the present invention of an integrated process for the production of methyl acetate and methanol.

FIG. 1 is a block diagram showing one embodiment of the present invention of an integrated process for the production of methyl acetate and methanol. The integrated unit 110 includes a synthesis gas feed line 112 and a dimethyl ether feed line 114 connected to a carbonylation reactor 116. The carbonylation reactor 116 contains a fixed bed of carbonylation catalyst, for example a mordenite zeolite, preferably H-mordenite. In use, fresh synthesis gas is heated to the desired carbonylation reaction temperature and fed to the carbonylation reactor 116 via synthesis gas feed line 112. The synthesis gas having a stoichiometric number in the range 0.9 to 1.3 comprises carbon monoxide, hydrogen and carbon dioxide. Dry dimethyl ether is fed to the carbonylation reactor 116 via dimethyl ether feed line 114. The dimethyl ether and synthesis gas are reacted in the presence of the catalyst in the carbonylation reactor 116 at a temperature in the range 250° C. to 350° C. and a total pressure in the range 10 to 100 barg (1000 kPa to 10000 kPa) to form a gaseous carbonylation reaction product comprising methyl acetate, unreacted dimethyl ether, a small amount of acetic acid and synthesis gas enriched in hydrogen. The carbonylation reaction product is withdrawn from the carbonylation reactor 116 via a carbonylation reaction product line 118, and fed to a separation unit 120 comprising, for example, a heat exchanger and knock-out drum. In separation unit 120, the carbonylation reaction product is cooled, preferably to a temperature in the range 40° C. to 50° C., and a methyl acetate-rich liquid stream comprising dimethyl ether and acetic acid, and a synthesis gas stream comprising dimethyl ether and residual amounts of methyl acetate are recovered from the separation unit 120. The methyl acetate-rich liquid stream is withdrawn from the separation unit 120 via a liquid product line 122. The synthesis gas stream is withdrawn from the separation unit 120 via a gaseous product line 124 and passed in its entirety to a scrubbing zone 126. The scrubbing zone 126 is supplied with a counter-current flow of liquid solvent, comprising methanol at a temperature suitably in the range 0° C. to 60° C., via a methanol feed line 128. The synthesis gas supplied to the scrubbing zone 126 is contacted therein with the methanol to remove methyl acetate, dimethyl ether and acetic acid. Methanol containing absorbed methyl acetate, dimethyl ether and acetic acid is withdrawn from the scrubbing zone 126 via a methanol removal line 130. The scrubbed synthesis gas depleted in methyl acetate and also depleted in acetic acid and dimethyl ether is withdrawn from the scrubbing zone 126 via a scrubbed feed line 132, heated in one or more heat exchangers (not shown) to the desired methanol synthesis temperature and passed to a methanol synthesis reactor 134. The methanol synthesis reactor 134 contains methanol synthesis catalyst, preferably a methanol synthesis catalyst comprising copper, such as a commercial Katalco™ methanol synthesis catalyst available from Johnson Matthey plc. Carbon monoxide, hydrogen and carbon dioxide are converted in the methanol synthesis zone 134 under methanol synthesis conditions, for example at a temperature in the range 230° C. to 275° C. and a total pressure of 50 to 100 barg (5000 kPa to 10,000 kPa), to a methanol synthesis product comprising methanol, unconverted synthesis gas and water, which methanol synthesis product is withdrawn from the methanol synthesis zone 134 via a methanol synthesis product line 136.

Figure 2:
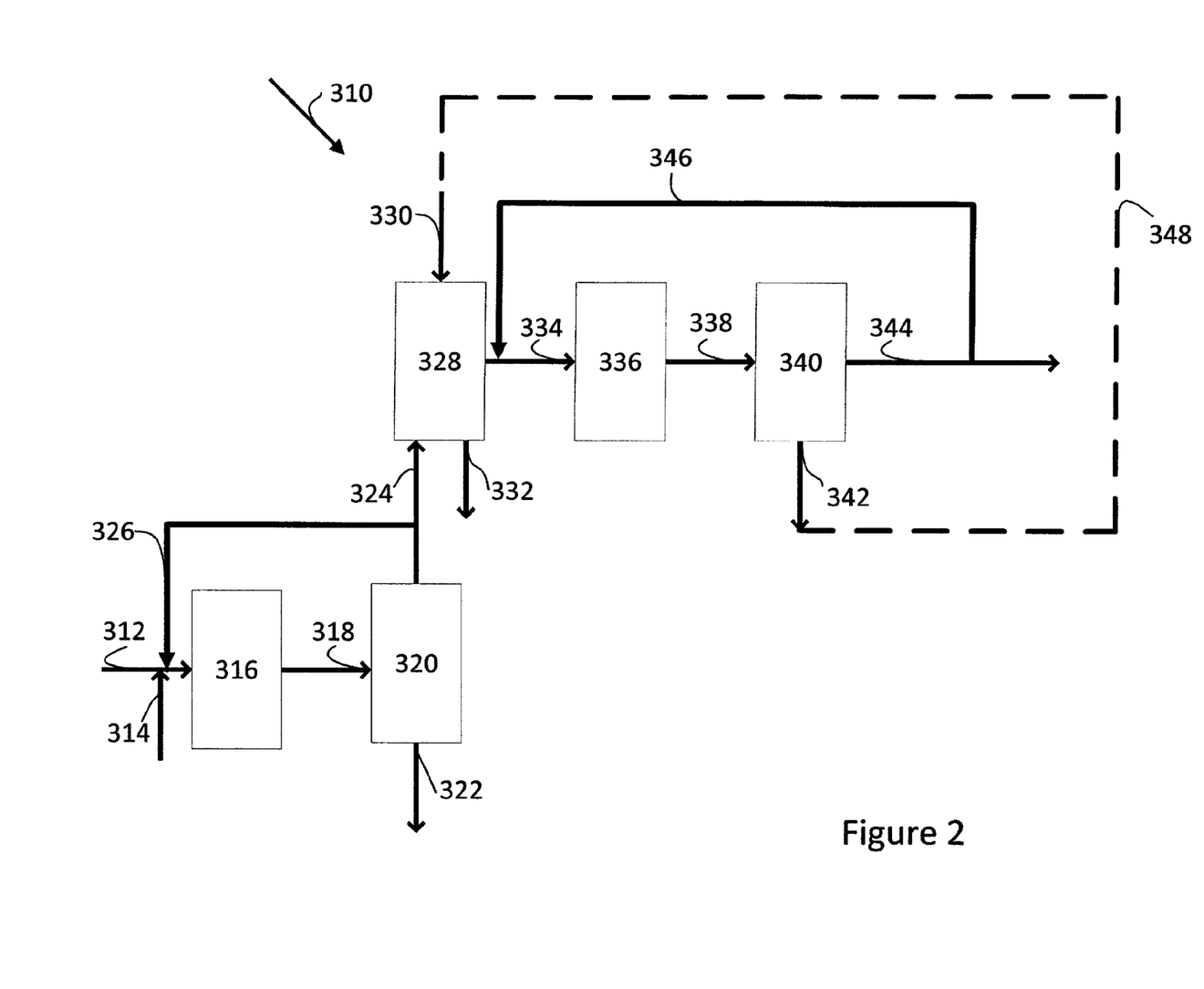
FIG. 2 is a block diagram showing an embodiment of the present invention of an integrated process for the production of methyl acetate and methanol and incorporating recycle of synthesis gas to the carbonylation reaction and methanol synthesis.

FIG. 2 shows an integrated unit for the production of methyl acetate and methanol 310, according to an embodiment of the present invention incorporating recycle of synthesis gas to the carbonylation reaction and methanol synthesis. The integrated unit 310 includes a synthesis gas feed line 312 and a dimethyl ether feed line 314 connected to a carbonylation reactor 316. The carbonylation reactor 316 contains a fixed bed of carbonylation catalyst, for example a mordenite zeolite, preferably mordenite in its hydrogen form. In use, fresh synthesis gas is heated to the desired carbonylation reaction temperature and fed to the carbonylation reactor 316 via synthesis gas feed line 312. The fresh synthesis gas has a stoichiometric number in the range 0.9 to 1.3 and comprises carbon monoxide, hydrogen and carbon dioxide. Dry dimethyl ether is fed to the carbonylation reactor 316 via dimethyl ether feed line 314. The dimethyl ether and synthesis gas are reacted in the presence of the catalyst in the carbonylation reactor 316 at a temperature in the range 250° C. to 350° C. and a total pressure in the range 10 to 100 barg (1000 kPa to 10,000 kPa) to form a gaseous carbonylation reaction product comprising methyl acetate, unreacted dimethyl ether, a small amount of acetic acid and synthesis gas enriched in hydrogen. The carbonylation reaction product is withdrawn from the carbonylation reactor 316 via a carbonylation reaction product line 318, and fed to a first separation unit 320 comprising, for example, a heat exchanger and knock-out drum. In first separation unit 320, the carbonylation reaction product is cooled, preferably to a temperature in the range 40° C. to 50° C., and a methyl acetate-rich liquid stream comprising dimethyl ether and acetic acid, and a synthesis gas stream comprising residual amounts of methyl acetate is recovered from the separation unit 320. The methyl acetate-rich liquid stream is withdrawn from the separation unit 320 via a liquid product line 322. The synthesis gas stream is withdrawn from the separation unit 320 via a gaseous product line 324, and is divided into a first and a second portion, for example by a suitable valve arrangement. The first portion of synthesis gas is supplied to a scrubbing zone 328 and the second portion of synthesis gas is recycled to the carbonylation reactor 316 via a synthesis gas recycle line 326, which joins the fresh synthesis gas feed line 312. The first synthesis gas portion comprises, for example, 20% to 30% of the synthesis gas and the second synthesis gas portion comprises, for example, 70% to 80% of the synthesis gas. The scrubbing zone 328 is supplied with a counter-current flow of liquid solvent comprising methanol at a temperature suitably in the range 0° C. to 60° C. via a methanol feed line 330. The synthesis gas supplied to the scrubbing zone 328 is contacted therein with the methanol to remove components soluble in methanol, such as methyl acetate, dimethyl ether and acetic acid. Methanol containing absorbed methyl acetate, dimethyl ether and acetic acid is withdrawn from the scrubbing zone 328 via a methanol removal line 332. The scrubbed synthesis gas depleted in methyl acetate and also depleted in acetic acid and dimethyl ether is withdrawn from the scrubbing zone 328 via a scrubbed feed line 334, heated in one or more heat exchangers (not shown) to the desired methanol synthesis temperature and passed to a methanol synthesis reactor 336. The methanol synthesis reactor 336 contains methanol synthesis catalyst, preferably a methanol synthesis catalyst comprising copper such as a Katalco™ catalyst available from Johnson Matthey plc. Carbon monoxide, hydrogen and carbon dioxide are converted in the methanol synthesis zone 336 under methanol synthesis conditions, for example at a temperature in the range 230° C. to 275° C. and a total pressure of 50 to 100 barg (5000 kPa to 10,000 kPa), to a gaseous methanol synthesis product comprising methanol, unconverted synthesis gas and water, which methanol synthesis product is withdrawn from the methanol synthesis zone 336 via a methanol synthesis product line 338. The methanol synthesis product is supplied to a second separation unit 340 comprising, for example, a heat exchanger and knock-out drum, where it is cooled to a temperature, suitably in the range 30° C. to 50° C., and a methanol-rich liquid stream comprising methanol and water, and a gaseous synthesis gas stream is recovered from the second separation unit 340. The methanol-rich liquid stream is withdrawn from the second separation unit 340 via a methanol product line 342. The synthesis gas is withdrawn from the second separation unit 340 via a synthesis gas line 344, and is divided into a first portion and a second portion, for example by a suitable valve system. The first portion of the synthesis gas is recycled to the methanol synthesis reactor via a synthesis gas recycle line 346, which joins synthesis gas line 334, so that the first portion of the synthesis gas is combined with the scrubbed synthesis gas, heated in one or more heat exchangers (not shown) and the combined synthesis gas stream is then passed to the methanol synthesis zone 336. The second portion of the synthesis gas is vented as a purge gas. The first portion of the synthesis gas (recycle synthesis gas) suitably comprises, for example, 95% to 99% of the synthesis gas, and the second portion of the synthesis gas (purge gas) suitably comprises, for example, 1% to 5% of the synthesis gas. Optionally some, and preferably all, of the methanol-rich liquid stream withdrawn from the second separation unit 340 is supplied to the scrubbing zone 328 via methanol supply line 348, which joins methanol feed line 330.

Figure 3:
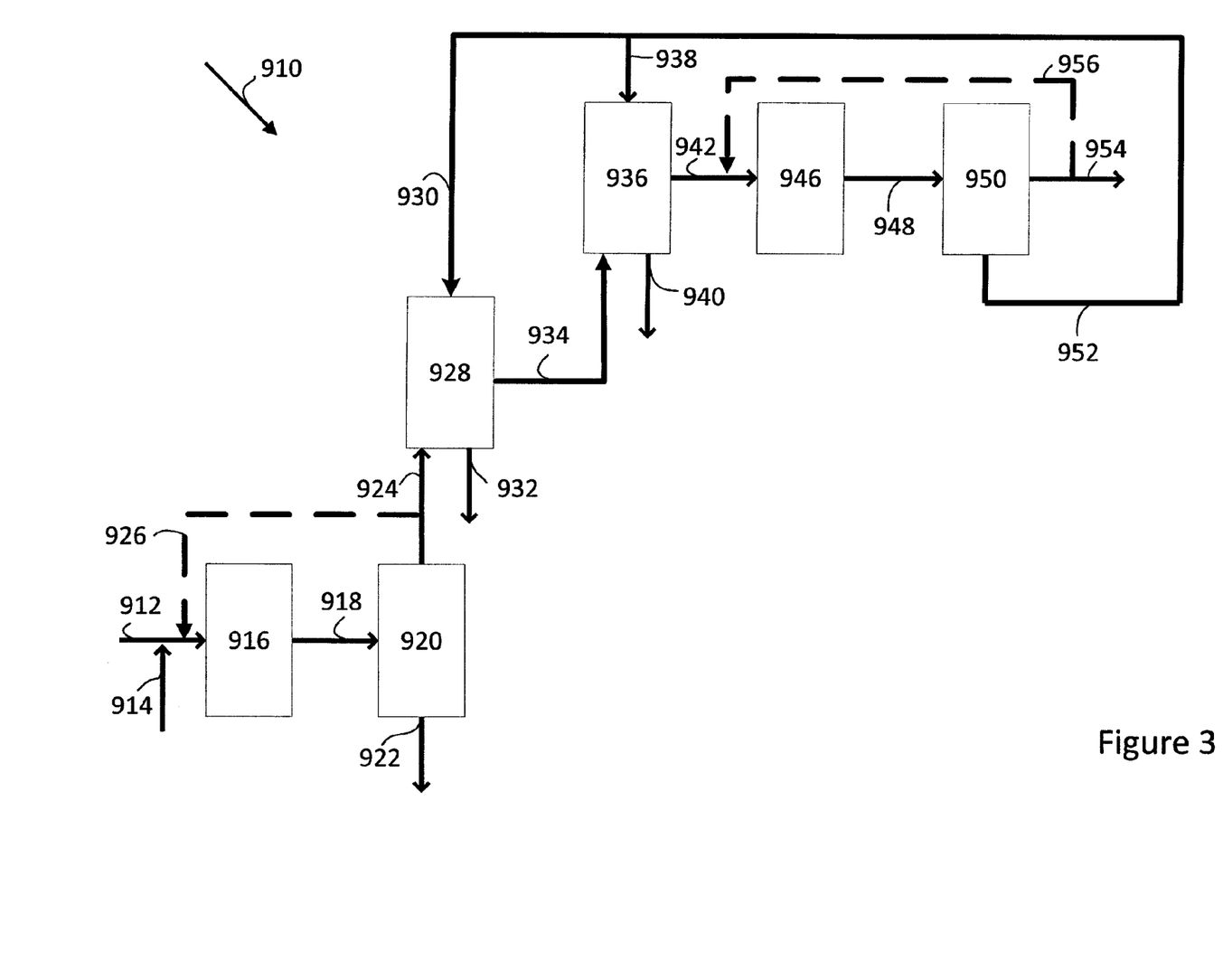
FIG. 3 is a block diagram showing an embodiment of the present invention of an integrated process for the production of methyl acetate and methanol and incorporating multiple scrubbing of synthesis gas.

FIG. 3 shows an integrated unit for the production of methyl acetate and methanol 910, according to an embodiment of the present invention incorporating multiple scrubbing of the synthesis gas recovered from the carbonylation reaction product. The integrated unit 910 includes a synthesis gas feed line 912 and a dimethyl ether feed line 914 connected to a carbonylation reactor 916. The carbonylation reactor 916 contains a fixed bed of carbonylation catalyst, for example a mordenite zeolite, preferably H-mordenite. In use, fresh synthesis gas is heated to the desired carbonylation reaction temperature and fed to the carbonylation reactor 916 via synthesis gas feed line 912. The synthesis gas having a stoichiometric number in the range 0.9 to 1.3 comprises carbon monoxide, hydrogen and carbon dioxide. Dry dimethyl ether is fed to the carbonylation reactor 916 via dimethyl ether feed line 914. The dimethyl ether and synthesis gas are reacted in the presence of the catalyst in the carbonylation reactor 916 at a temperature in the range 250° C. to 350° C. and a total pressure in the range 10 to 100 barg (1000 kPa to 10,000 kPa) to form a gaseous carbonylation reaction product comprising methyl acetate, unreacted dimethyl ether, a small amount of acetic acid and synthesis gas enriched in hydrogen. The carbonylation reaction product is withdrawn from the carbonylation reactor 916 via a carbonylation reaction product line 918, and fed to a separation unit 920 comprising, for example, a heat exchanger and knock-out drum. In separation unit 920, the carbonylation reaction product is cooled, preferably to a temperature in the range 40° C. to 50° C., and a methyl acetate-rich liquid stream comprising dimethyl ether and acetic acid, and a gaseous synthesis gas stream comprising residual amounts of methyl acetate is recovered from the separation unit 920. The methyl acetate-rich liquid stream is withdrawn from the separation unit 920 via a liquid product line 922. The synthesis gas stream is withdrawn from the separation unit 920 via a gaseous product line 924, and at least a portion of the synthesis gas is supplied to a first scrubbing unit 928. All of the synthesis gas withdrawn from the separation unit 920 may be supplied to the first scrubbing unit 928, but preferably, the synthesis gas stream is divided and a portion of the synthesis gas is recycled to the carbonylation reaction via a synthesis gas recycle line 926. Where the synthesis gas is divided, suitably 15% to 25% of the synthesis gas is supplied to the first scrubbing unit 928 and 75% to 85% of the synthesis gas is recycled to the carbonylation reaction. The first scrubbing unit 928 is supplied with a counter-current flow of liquid solvent comprising methanol at a temperature suitably in the range 0° C. to 60° C. via a methanol feed line 930. The synthesis gas supplied to the scrubbing unit 928 is contacted therein with the methanol to remove components soluble in methanol, such as methyl acetate, dimethyl ether and acetic acid. Methanol containing absorbed methyl acetate, dimethyl ether and acetic acid is withdrawn from the scrubbing unit 928 via a methanol removal line 932. The scrubbed synthesis gas depleted in methyl acetate and also depleted in acetic acid and dimethyl ether is withdrawn from the scrubbing unit 928 via a first scrubbed synthesis gas line 934. The scrubbed synthesis gas stream is supplied to a second scrubbing unit 936. The second scrubbing unit 936 is supplied with a counter-current flow of liquid solvent comprising methanol at a temperature suitably in the range 0° C. to 60° C. via a methanol feed line 938. The scrubbed synthesis gas supplied to the second scrubbing unit 936 is contacted therein with the methanol to further reduce the methyl acetate, dimethyl ether and acetic acid content of the synthesis gas. A second liquid solvent stream of methanol containing absorbed methyl acetate, dimethyl ether and acetic acid is withdrawn from the second scrubbing unit 936 via a second methanol removal line 940. Synthesis gas further depleted in methyl acetate is withdrawn from the second scrubbing unit 936 via a second scrubbed synthesis gas line 942. As methyl acetate is particularly soluble in methanol, most of the methyl acetate contained in the synthesis gas provided to the first scrubbing unit 928 will be removed therefrom and is absorbed in the liquid methanol stream removed from the first scrubbing unit 928 via the first liquid solvent line 932. However, some methyl acetate may remain in the scrubbed synthesis gas supplied to the second scrubbing unit 936, most of which is absorbed in the second liquid methanol stream. The synthesis gas stream withdrawn from the second scrubbing unit 936 is heated in one or more heat exchangers (not shown) to the desired methanol synthesis temperature and passed to a methanol synthesis reactor 946 via the second synthesis gas line 942. The methanol synthesis reactor 946 contains a methanol synthesis catalyst, preferably a methanol synthesis catalyst comprising copper, such as a Katalco™ catalyst, available from Johnson Matthey plc. Carbon monoxide, hydrogen and carbon dioxide are converted in the methanol synthesis reactor 946 under methanol synthesis conditions, for example at a temperature in the range 230° C. to 275° C. and a total pressure of 50 to 100 barg (5000 kPa to 10,000 kPa), to a gaseous methanol synthesis product comprising methanol, unconverted synthesis gas and water, which methanol synthesis product is withdrawn from the methanol synthesis reactor 946 via a methanol synthesis product line 948. The methanol synthesis product is supplied to a second separation unit 950 comprising, for example, a heat exchanger and knock-out drum, where it is cooled to a temperature, suitably in the range 30° C. to 50° C., and a methanol-rich liquid stream comprising methanol and water, and a gaseous synthesis gas stream is recovered from the second separation unit 950. The methanol-rich liquid stream is withdrawn from the second separation unit 950 via a methanol product line 952 and is supplied to the first and second scrubbing units 928 and 936. The relative amounts of the methanol-rich liquid stream supplied to each of the two scrubbing units 928 and 936 may vary; however, preferably a minor portion, for example 10%, is supplied to the first scrubbing unit 928 via first methanol feed line 930, and a major portion, for example 90%, is supplied to the second scrubbing unit 936 via second methanol feed line 938. The synthesis gas stream is withdrawn from the second separation unit 950 via a synthesis gas line 954. The synthesis gas may be vented as a purge stream. Optionally, the synthesis gas stream may be divided and a portion thereof recycled to the methanol synthesis reaction via optional synthesis gas recycle line 956. Where the synthesis gas stream is divided, suitably 95% to 99% of it may be recycled to the methanol synthesis reactor 946, and 1 to 5% of it may be vented as the purge stream. The first liquid solvent stream comprising methanol and absorbed methyl acetate, dimethyl ether and acetic acid withdrawn from the first scrubbing unit 928, and the second liquid solvent stream comprising methanol and any absorbed methyl acetate, dimethyl ether and acetic acid withdrawn from the second scrubbing unit 936, may be combined or may be separately processed (not shown).

The invention is now illustrated with reference to the following non-limiting Examples.

EXAMPLE 1

This Example demonstrates an integrated process for the production of methyl acetate and methanol, wherein a gaseous stream obtained from the carbonylation of dimethyl ether to produce methyl acetate is used as the feed to the methanol synthesis. Reference is made to FIG. 1 and Table 1 which summarises the results of the relevant process streams.

A synthesis gas comprising hydrogen, carbon monoxide and carbon dioxide with a hydrogen:carbon monoxide molar ratio of 1.15 and a stoichiometric number (SN) of 1.07, and comprising trace quantities of inert gases (Synthesis Gas Feed), is fed to the carbonylation reactor. Dimethyl ether (DME Feed) is supplied to the carbonylation reactor. The synthesis gas and dimethyl ether are reacted therein in the presence of a H-mordenite zeolite catalyst under reaction conditions effective to catalyse the carbonylation of the dimethyl ether to produce methyl acetate, for example at a temperature in the range 250° C. to 350° C. and a total pressure in the range 10 to 100 barg (1000 kPa to 10,000 kPa). A gaseous carbonylation reaction product comprising methyl acetate and synthesis gas enriched in hydrogen is withdrawn from the carbonylation reactor, cooled and passed to a gas/liquid separator to recover a liquid stream comprising mainly methyl acetate (Methyl Acetate Product Stream) together with lesser amounts of dimethyl ether and acetic acid, and a gaseous stream comprising synthesis gas, residual amounts of methyl acetate, dimethyl ether and acetic acid (Scrubber Feed). This gaseous stream has a stoichiometric number of 2.02, and is supplied to a scrubbing column of conventional design, where it is contacted counter-currently with liquid methanol to obtain a liquid methanol stream comprising absorbed methyl acetate, dimethyl ether and acetic acid, and a synthesis gas stream depleted in methyl acetate of stoichiometric number 2.04. The scrubbed synthesis gas stream (Methanol Synthesis Feed) is heated to the methanol synthesis temperature and passed to a conventional methanol synthesis reactor. The methanol synthesis is a low pressure synthesis operating at a total pressure of 50 to 100 barg (5000 kPa to 10,000 kPa), a temperature of from 240° C. to 275° C. and using a methanol synthesis catalyst comprising copper, such as a Katalco™ methanol synthesis catalyst commercially available from Johnson Matthey plc, to produce a methanol synthesis product stream (Methanol Product) comprising methanol, unconverted synthesis gas and dimethyl ether. Examples of the molar flow rates of the process streams in the integrated process are given in Table 1 below.

TABLE 1

| Molar Flow per unit time | Synthesis Gas Feed | DME Feed | Methyl Acetate Product | Scrubber Feed | Methanol Synthesis Feed | Methanol Product |
|---|---|---|---|---|---|---|
| Hydrogen | 2323.0 | 0.0 | 5.9 | 2277.1 | 2264.0 | 251.0 |
| Methane | 0.0 | 0.0 | 0.5 | 39.5 | 39.0 | 39.0 |
| Nitrogen | 101.0 | 0.0 | 0.5 | 100.5 | 100.0 | 100.0 |
| Carbon monoxide | 2020.0 | 0.0 | 5.5 | 1014.5 | 1006.1 | 19.1 |
| Water | 0.0 | 0.2 | 2.5 | 1.6 | 0.3 | 13.3 |
| Carbon dioxide | 80.8 | 0.0 | 6.6 | 74.2 | 68.4 | 55.4 |
| Methanol | 0.0 | 1.5 | 14.9 | 2.7 | 31.9 | 1031.9 |
| Methyl acetate | 0.0 | 0.0 | 827.0 | 157.1 | 0.0 | 0.0 |
| Dimethyl ether | 0.0 | 1500.0 | 161.6 | 318.4 | 93.6 | 93.6 |
| Acetic acid | 0.0 | 0.0 | 15.6 | 0.4 | 0.0 | 0.0 |
| Total | 4524.8 | 1501.7 | 1040.6 | 3986.0 | 3603.3 | 1603.3 |
| $H_2$:CO | 1.15 | | | 2.24 | 2.25 | |
| Stoichiometric number (SN) | 1.07 | | | 2.02 | 2.04 | |

EXAMPLE 2

This Example demonstrates an integrated process for the production of methyl acetate and methanol, wherein a gaseous stream obtained from the carbonylation of dimethyl ether to produce methyl acetate is used as the feed to the methanol synthesis and wherein the product stream obtained from the methanol synthesis is separated into a liquid stream comprising mainly methanol and a synthesis gas stream.

The process of Example 1 is repeated using a synthesis gas feed (Synthesis Gas Feed) and a dimethyl ether feed (DME Feed) having the compositions set out in Table 2.

The product stream from the methanol synthesis reactor is fed to a separation unit, comprising a heat exchanger and a knock-out drum, and cooled and separated into a liquid stream comprising mainly methanol (Methanol Product) and a gaseous synthesis gas stream (Methanol Synthesis Gas) comprising dimethyl ether.

Examples of the molar flow rates that may be obtained in the above integrated process are given in Table 2 below.

metric number of this synthesis gas stream is 2.04. The synthesis gas stream is split into two streams, with approximately 76% of the synthesis gas stream (Recycle syngas stream (to Carb)) being recycled to the fresh synthesis gas feed to produce a combined feed (Total Feed (to Carb)), and approximately 24% of the synthesis gas stream (Scrubber Feed) being supplied to a conventional gas/liquid scrubbing unit, where it is counter-currently contacted with an aqueous methanol recycle stream (Methanol Liquid Stream) to obtain a synthesis gas depleted in methyl acetate. The methanol liquid stream containing absorbed methyl acetate and other components (Scrubber Outflow) is withdrawn from the scrubbing unit. A scrubbed synthesis gas (Scrubbed Syngas Feed) is withdrawn from the scrubbing unit, heated to the methanol synthesis temperature and passed to a conventional methanol synthesis zone in combination with a recycle synthesis gas stream (Recycle Syngas (to Methanol)) from the methanol synthesis zone, to form a combined

TABLE 2

| Molar Flow per unit time | Synthesis Gas Feed | DME Feed | Methyl Acetate Product | Scrubber Feed | Methanol Synthesis Feed | Methanol Product | Methanol Synthesis Gas |
|---|---|---|---|---|---|---|---|
| Hydrogen | 2323.0 | 0.0 | 5.9 | 2277.1 | 2264.0 | 0.3 | 250.7 |
| Methane | 0.0 | 0.0 | 0.5 | 39.5 | 39.0 | 0.2 | 38.8 |
| Nitrogen | 101.0 | 0.0 | 0.5 | 100.5 | 100.0 | 0.1 | 99.9 |
| Carbon monoxide | 2020.0 | 0.0 | 5.5 | 1014.5 | 1006.1 | 0.0 | 19.1 |
| Water | 0.0 | 0.2 | 2.5 | 1.6 | 0.3 | 12.7 | 0.6 |
| Carbon dioxide | 80.8 | 0.0 | 6.6 | 74.2 | 68.4 | 1.3 | 54.1 |
| Methanol | 0.0 | 1.5 | 14.9 | 2.7 | 31.9 | 952.0 | 79.9 |
| Methyl acetate | 0.0 | 0.0 | 827.0 | 157.1 | 0.0 | 0.0 | 0.0 |
| Dimethyl ether | 0.0 | 1500.0 | 161.6 | 318.4 | 93.6 | 26.1 | 67.5 |
| Acetic acid | 0.0 | 0.0 | 15.6 | 0.4 | 0.0 | 0.0 | 0.0 |
| Total | 4524.8 | 1501.7 | 1040.6 | 3986.0 | 3603.3 | 992.7 | 610.6 |
| $H_2$:CO | 1.15 | | | 2.24 | 2.25 | | |
| Stoichiometric number (SN) | 1.07 | | | 2.02 | 2.04 | | |

EXAMPLE 3

This Example demonstrates an integrated process for the production of methyl acetate and methanol, wherein part of the synthesis gas stream recovered from the carbonylation of dimethyl ether to produce methyl acetate is used as the synthesis gas feed to methanol synthesis. FIG. 2 shows the basic components suitable for carrying out the integrated process of this Example. The carbonylation reaction detailed in Example 1 is repeated using a synthesis gas feed (Syngas Feed) and a dimethyl ether feed (DME Feed) having the compositions set out in Table 3. The synthesis gas has a hydrogen:carbon monoxide molar ratio of 1.13 and a stoichiometric number (SN) of 1.03. The synthesis gas and the dimethyl ether feed are combined before being supplied to the carbonylation reaction. The gaseous product stream withdrawn from the carbonylation reactor (Product Stream (Carb)) is supplied to a separation unit and cooled and separated therein to recover a methyl acetate-rich liquid stream (MeOAc Liquid Stream) and a gaseous synthesis gas stream comprising unreacted dimethyl ether, methyl acetate and acetic acid (Syngas Stream (from Carb)). The stoichiosynthesis gas stream (Total Syngas Feed (to Methanol)). The combined synthesis gas stream passed to the methanol synthesis zone is contacted therein with a copper-containing methanol synthesis catalyst commercially available from Johnson Matthey plc, for example a Katalco™ catalyst. The methanol synthesis is a low pressure synthesis operated at a temperature of from 240° C. to 275° C. and a total pressure of 50 to 100 barg (5000 kPa to 10,000 kPa), to produce a product stream comprising methanol (Total Product Stream (from Methanol)). The product stream is withdrawn from the methanol synthesis zone and provided to a conventional separation unit comprising a heat exchanger and a knockout drum, to cool and recover from the product stream a methanol-rich liquid stream (Methanol Liquid Stream) and a gaseous synthesis gas stream (Methanol Syngas Stream). The methanol-rich liquid stream is returned to the scrubbing unit. Approximately 2% of the synthesis gas stream is vented as a purged gas (Methanol Purge) and the remaining portion (approximately 98%) of the synthesis gas stream is recycled to the methanol synthesis (the Recycle Syngas (to Methanol)).

Examples of the molar flow rates that may be obtained in the above combined process are given in Table 3 below.

TABLE 3

|   | Syngas Feed | DME Feed | Recycle Syngas Stream (to Carb) | Total Feed (to Carb) | Product Stream (Carb) | MeOAc Liquid Stream | Syngas Stream (from Carb) | Scrubber Feed |
|---|---|---|---|---|---|---|---|---|
| $H_2$ | 225.64 | 0.00 | 701.56 | 927.20 | 923.19 | 2.40 | 920.79 | 219.24 |
| $CH_4$ | 1.99 | 0.00 | 18.19 | 20.18 | 24.18 | 0.30 | 23.88 | 5.69 |
| $N_2$ | 0.99 | 0.00 | 3.12 | 4.11 | 4.11 | 0.02 | 4.09 | 0.98 |
| CO | 198.80 | 0.00 | 309.16 | 507.96 | 407.96 | 2.19 | 405.77 | 96.61 |
| $H_2O$ | 0.00 | 0.01 | 0.14 | 0.14 | 0.46 | 0.28 | 0.18 | 0.04 |
| $CO_2$ | 9.94 | 0.00 | 23.17 | 33.11 | 33.11 | 2.70 | 30.41 | 7.24 |
| MeOH | 0.00 | 0.12 | 0.24 | 0.36 | 2.05 | 1.74 | 0.31 | 0.07 |
| MeOAc | 0.00 | 0.00 | 13.61 | 13.61 | 113.92 | 94.06 | 17.86 | 4.25 |
| DME | 0.00 | 121.50 | 19.93 | 141.43 | 39.43 | 13.27 | 26.16 | 6.23 |
| Acetic Acid | 0.00 | 0.00 | 0.03 | 0.03 | 1.72 | 1.68 | 0.04 | 0.01 |
| Total | 437.36 | 121.63 | 1089.15 | 1648.13 | 1548.13 | 118.64 | 1429.49 | 340.36 |
| $H_2$:CO | 1:13 |  | 2.27 | 1.83 | 2.26 |  | 2.27 |  |
| SN | 1.03 |  | 2.04 | 1.65 | 2.02 |  | 2.04 |  |

|   | Methanol Liquid Stream | Scrubber Outflow | Scrubbed Syngas Feed | Recycle Syngas Feed (to Methanol) | Total Syngas Feed (to Methanol) | Total Product Stream (from Methanol) | Methanol Syngas Stream | Methanol Purge |
|---|---|---|---|---|---|---|---|---|
| $H_2$ | 0.83 | 1.30 | 218.77 | 599.73 | 818.50 | 612.79 | 611.96 | 12.23 |
| $CH_4$ | 1.44 | 0.13 | 7.00 | 272.03 | 279.03 | 279.03 | 277.59 | 5.56 |
| $N_2$ | 0.07 | 0.01 | 1.04 | 47.46 | 48.50 | 48.49 | 48.42 | 0.96 |
| CO | 0.14 | 0.81 | 95.94 | 73.53 | 169.47 | 75.17 | 75.03 | 1.50 |
| $H_2O$ | 5.80 | 5.74 | 0.10 | 0.24 | 0.34 | 6.05 | 0.25 | 0.01 |
| $CO_2$ | 0.91 | 0.76 | 7.39 | 38.20 | 45.59 | 39.90 | 38.99 | 0.79 |
| MeOH | 103.27 | 99.90 | 3.44 | 8.49 | 11.93 | 111.94 | 8.67 | 0.18 |
| MeOAc | 0.00 | 4.25 | 0.00 | 0.00 | 0.00 | 0.00 | 0.00 | 0.00 |
| DME | 2.17 | 6.12 | 2.28 | 5.48 | 7.76 | 7.77 | 5.60 | 0.12 |
| Acetic Acid | 0.00 | 0.01 | 0.00 | 0.00 | 0.00 | 0.00 | 0.00 | 0.00 |
| Total | 114.63 | 119.03 | 335.96 | 1045.16 | 1381.12 | 1181.14 | 1066.51 | 21.35 |
| $H_2$:CO |  |  | 2.28 | 8.16 | 4.83 |  |  |  |
| SN |  |  | 2.04 | 5.03 | 3.59 |  |  |  |

The abbreviations used in Table 3 have the following meanings:
DME is dimethyl ether
MeOH is methanol
MeOAc is methyl acetate
SN is stoichiometric number

EXAMPLE 4

This Example investigates the effect of methyl acetate on methanol synthesis from synthesis gas. Pellets of Katalco™ methanol catalyst (Johnson Matthey plc) were crushed and sieved to a size-fraction of 125-160 microns. A tubular reactor of 9 mm internal diameter was charged with 3 ml of the catalyst diluted 1:1 v/v with quartz chips. The length of the catalyst bed was 100 mm. In Runs 1, 3, 4 and 6 synthesis gas of composition 62 mol % $H_2$, 7 mol % CO, 5 mol % $CO_2$, 21 mol % $N_2$ and 5 mol % Ar was fed to the reactor at total gas hourly space velocities (GHSV) of 5000 $h^{-1}$ and 20000 $h^{-1}$ under conditions of a total pressure of 75 bar (7500 kPa) and a temperature of 260° C. The experiments were repeated in Runs 2 and 5 using synthesis gas of composition 62 mol % $H_2$, 7 mol % CO, 5 mol % $CO_2$, 20 mol % $N_2$ and 5 mol % Ar and a co-feed of 1 mol % methyl acetate. In each experiment the exit stream frdm the reactor was passed to two gas chromatographs (GC's) for analysis of the components of the exit stream. The GC's were a Varian 4930 micro GC with three columns (molecular sieve 5A, Porapak® Q and CP-Wax-52), each column equipped with a thermal conductivity detector and an Interscience trace GC with two columns (CP Sil 5 and CP-Wax-52), each column equipped with a flame ionization detector. Table 4 below provides the space time yields (STY) in grams of methanol product per liter of catalyst per hour and selectivities (Sel) to methanol achieved for each of the experiments. The data in Table 4 clearly demonstrates that the production of methanol from synthesis gas is adversely affected by the presence of methyl acetate.

TABLE 4

| Run No. | Methyl acetate/ mol % | Temp/ ° C. | Time on stream/ hrs | GHSV/ $h^{-1}$ | Sel/% | STY/ g/l · h |
|---|---|---|---|---|---|---|
| 1 | 0 | 260 | 74 | 20000 | 99.9 | 1335 |
| 2 | 1 | 260 | 51 | 20000 | 95.7 | 803 |
| 3 | 0 | 260 | 44 | 20000 | 99.9 | 1041 |
| 4 | 0 | 260 | 74 | 5000 | 99.0 | 407 |
| 5 | 1 | 260 | 51 | 5000 | 96.0 | 364 |
| 6 | 0 | 260 | 44 | 5000 | 99.0 | 409 |

The invention claimed is:
1. An integrated process for the production of methyl acetate and methanol which process comprises:
(i) feeding synthesis gas and dimethyl ether into a carbonylation reaction zone and reacting therein the synthesis gas and dimethyl ether in the presence of a carbonylation catalyst to form a gaseous carbonylation reaction product comprising methyl acetate and synthesis gas enriched in hydrogen relative to the hydrogen content of the feed synthesis gas and wherein the carbonylation catalyst is an aluminosilicate zeolite which comprises at least one channel which is defined by an 8-membered ring;

(ii) withdrawing carbonylation reaction product from the carbonylation reaction zone and recovering therefrom a methyl acetate-rich liquid stream and a synthesis gas stream comprising residual amounts of methyl acetate; and wherein the synthesis gas is split into a major portion and a minor portion;

(iii) scrubbing in a scrubbing zone the minor portion of the synthesis gas recovered from the carbonylation reaction product with a liquid scrubbing solvent to reduce the content of the methyl acetate in the synthesis gas and to obtain a scrubbed synthesis gas depleted in methyl acetate and a liquid solvent stream comprising methyl acetate;

(iv) passing scrubbed synthesis gas to a methanol synthesis zone and contacting it therein with a methanol synthesis catalyst to form a methanol synthesis product comprising methanol and unconverted synthesis gas; and wherein the major portion of the synthesis gas recovered from the carbonylation reaction product is recycled to the carbonylation reaction zone.

2. A process according to claim 1 which further comprises the steps of (v) withdrawing methanol synthesis product from the methanol synthesis zone and recovering therefrom a methanol-rich liquid stream and a synthesis gas stream; and (vi) recycling at least a portion of the synthesis gas stream recovered from the methanol synthesis product to the methanol synthesis zone.

3. A process according to claim 1 wherein the scrubbed synthesis gas is passed to the methanol synthesis zone as a combined feed with at least a portion of synthesis gas recovered from the methanol synthesis product.

4. A process according to claim 1 wherein the synthesis gas fed to the carbonylation reaction zone is fresh synthesis gas having a stoichiometric number SN and $SN=(H_2-CO_2)/(CO+CO_2)$ in the range 0.9 to 1.3.

5. A process according to claim 4 wherein the stoichiometric number of the fresh synthesis gas is lower than the stoichiometric number of the scrubbed synthesis gas passed to the methanol synthesis zone.

6. A process according to claim 1 wherein the scrubbed synthesis gas has a stoichiometric number in the range 1.5 to 2.5.

7. A process according to claim 6 wherein the stoichiometric number is in the range 2.0 to 2.1.

8. A process according to claim 1 wherein the synthesis gas feed to the carbonylation reaction zone is fresh synthesis gas or a mixture of fresh and recycle synthesis gas.

9. A process according to claim 1 wherein the synthesis gas feed (including any recycles) to the carbonylation reaction zone comprises carbon dioxide.

10. A process according to claim 9 wherein carbon dioxide is present in the synthesis gas in an amount in the range 0.5 to 12 mol %.

11. A process according to claim 1 wherein the aluminosilicate zeolite has a framework structure type selected from MOR, FER, OFF and GME.

12. A process according to claim 11 wherein the zeolite has a framework structure type MOR and is a mordenite.

13. A process according to claim 1 wherein the synthesis gas and dimethyl ether are reacted in the carbonylation reaction zone under conditions of a temperature in the range 250° C. to 350° C. and a total pressure in the range 50 to 100 barg (5000 kPa to 10,000 kPa).

14. A process according to claim 1 wherein the major portion is 70 to 80 mol % of the synthesis gas recovered from the carbonylation reaction product.

15. A process according to claim 1 wherein synthesis gas recovered from the carbonylation reaction product comprises methyl acetate in an amount in the range 0.1 to 5 mol %.

16. A process according to claim 1 wherein the scrubbing solvent comprises methanol.

17. A process according to claim 16 wherein the scrubbing solvent further comprises one or more of water and dimethyl ether.

18. A process according to claim 1 wherein synthesis gas recovered from the carbonylation reaction product is subjected to multiple scrubbings.

19. A process according to claim 18 wherein the multiple scrubbings are conducted in one scrubbing unit.

20. A process according to claim 2 wherein the scrubbing solvent is at least a portion of the methanol-rich liquid stream recovered from the methanol synthesis product.

21. A process according to claim 1 wherein the scrubbed synthesis gas has a stoichiometric number in the range 1.5 to 2.5.

22. A process according to claim 1 wherein the methanol synthesis catalyst comprises copper.

23. A process according to claim 1 wherein synthesis gas is contacted with the methanol synthesis catalyst under conditions of a temperature of from 210° C. to 270° C. and a total pressure in the range 50 to 100 barg (5000 kPa to 10,000 kPa).

24. A process according to claim 1 wherein methanol is recovered from one or more of the methanol synthesis product withdrawn from the methanol synthesis zone and liquid solvent streams comprising methanol obtained from scrubbing of synthesis gas recovered from the carbonylation reaction product.

25. A process according to claim 2 wherein methanol is recovered from the methanol-rich liquid stream recovered from the methanol synthesis product.

26. A process according to claim 2 wherein methyl acetate is recovered from at least a portion of the methyl acetate-rich liquid stream and the recovered methyl acetate is converted to acetic acid.

27. A process according to claim 1 wherein recovered methyl acetate is converted to acetic acid by hydrolysis.

28. A process according to claim 1 wherein a portion of the synthesis gas recovered from the methanol synthesis product is vented as a purge stream.

29. A process according to claim 1 wherein in each of the carbonylation reaction zone and the methanol synthesis zone the reaction is conducted as a heterogeneous vapour phase reaction.

30. A process according to claim 1 wherein the process is operated as a continuous process.

* * * * *